US005649998A

United States Patent [19]

Ungerer et al.

[11] Patent Number: 5,649,998
[45] Date of Patent: Jul. 22, 1997

[54] DEVICE FOR SEPARATING THE PHASES OF A FLUID SAMPLE

[75] Inventors: Philippe Ungerer, Creteil; Gérard Moracchini, Andilly; José Sanchez, Viarmes, all of France

[73] Assignee: Institut Francais du Petrole, Rueil Malmaison, France

[21] Appl. No.: 591,912

[22] Filed: Jan. 25, 1996

Related U.S. Application Data

[63] Continuation of Ser. No. 257,708, Jun. 10, 1994, abandoned.

[30] Foreign Application Priority Data

Jun. 11, 1993 [FR] France .................................. 93 07078

[51] Int. Cl.⁶ .................................................. B01D 19/00
[52] U.S. Cl. .................................. 96/209; 96/204; 96/208; 96/216
[58] Field of Search .......................... 96/204, 208, 209, 96/216

[56] References Cited

U.S. PATENT DOCUMENTS 3,243,941  4/1966  Peterson .
4,713,095  12/1987  Ricciardelli .

FOREIGN PATENT DOCUMENTS

| 1295829 | 5/1962 | France . |
| 2621051 | 12/1977 | Germany . |
| 4118639 | 12/1992 | Germany . |
| 1520520 | 8/1978 | United Kingdom . |
| 2021445 | 12/1979 | United Kingdom . |
| 2254024 | 9/1992 | United Kingdom . |

OTHER PUBLICATIONS

Patent Abstracts of Japan, vol. 13, No. 255 (date uncertain).

*Primary Examiner*—Romulo H. Delmendo
*Attorney, Agent, or Firm*—Antonelli, Terry, Stout & Kraus, LLP

[57] ABSTRACT

A cyclone separating device includes a transparent and tapered separator flask, with an upper outlet where a tube provided with seal means and a tubular extension is fastened, and a lateral inlet through a lateral appendix communicating with the inside of the flask through a fine channel offset in order to generate a cyclone effect promoting the separation of the phases and lined with an insert made of a plastic material. The fluid sample is injected, for example, through a septum by means of a hollow needle guided through the insert. The device can be used for processing geologic fluid samples.

19 Claims, 3 Drawing Sheets

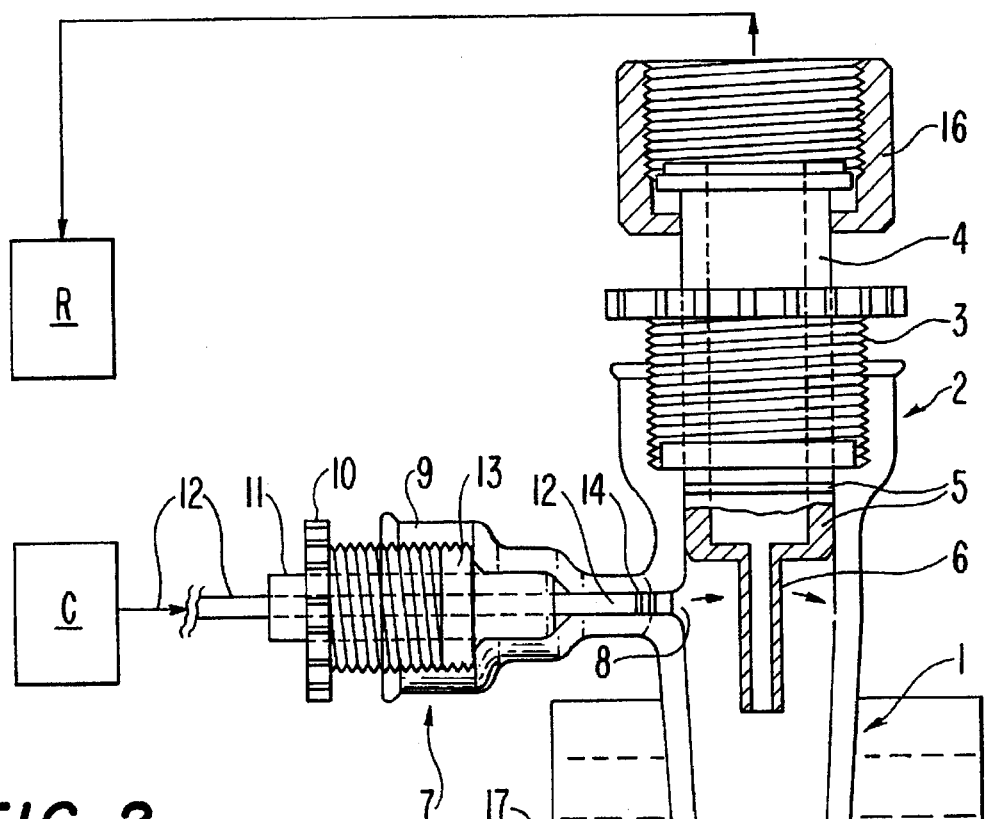
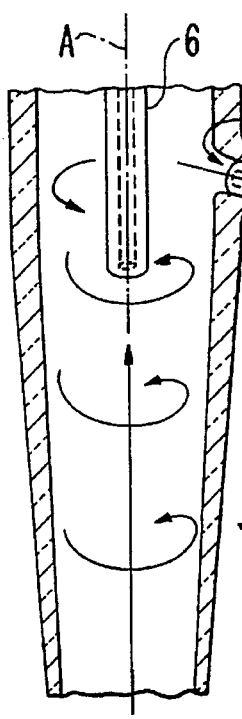

DEVICE FOR SEPARATING THE PHASES OF A FLUID SAMPLE

This application is a continuation application of U.S. patent application Ser. No. 257,708, filed Jun. 10, 1994, now abandoned.

FIELD OF THE INVENTION

The object of the present invention is to propose a device for separating from one another the phases of a two-phase fluid, which is well suited for measuring with precision the liquid phase after the separation thereof.

The separating device according to the invention is particularly adapted for separating the phases of fluid samples of low volume such as those which are for example processed within the scope of analyses concerning geologic samples taken in boreholes through subsoil reservoirs containing petroleum effluents.

BACKGROUND OF THE INVENTION

Patent application FR-93/07,077 filed by the applicant describes a transfer system for taking in balancing cells samples kept at high pressures analogous to those prevailing in subsoil formations where they have been initially taken. This system includes a sampling cell withstanding pressures higher than 100 MPa and temperatures of several hundred degrees above or below 0° C., suited for sampling small amounts (of the order of several $cm^3$) of fluid samples under pressure. The fluids contained in the sampling cell are transferred into measuring devices in order to be measured and analyzed. The fluid may for example be expanded with a change in the temperature thereof, so as to measure under standard pressure and temperature conditions the proportion of liquid and gaseous volume. To that effect notably, the two phases have to be separated properly.

A separating device generally includes a vessel with a lateral inlet for the injection of a two-phase mixture, placed above the level likely to be reached by the liquid phase and a separation space. The gas phase flows out through an upper port whereas the liquid phase is collected at the base of the vessel.

It is known to offset the lateral inlet port with respect to the axis of the flask so as to obtain a cyclone effect and a centrifugal force which drives the liquid phase of the sample away from the upper port, which facilitates the separation of the phases of the injected fluid.

Such a separating device is for example described in U.S. Pat. No. 4,713,095.

SUMMARY OF THE INVENTION

The device according to the invention is designed to obtain a perfect separation of a gas phase and of a liquid phase in a sample containing at least two phases. It includes a flask provided with a lateral inlet for the injection of the sample, this lateral inlet being offset so as to facilitate the separation of the phases, and with an upper port (2) for the escape of the gas phase from the flask.

It comprises a fine tubular element communicating at a first end with the inside of the flask and at another end with a vessel containing said substance, the inner section of this tubular element being so selected that most of the pressure drop undergone by the injected sample occurs along the tubular element, the flask being made of a substantially transparent material.

The device includes for example a tube provided with seal means, which is engaged in the upper port and extended towards the inside of the flask by a tubular extension arranged substantially along the axis of the flask, whose section is sufficient for the pressure drop to be negligible with respect to the pressure drop in said fine tubular element, and means for fastening the tube to the flask. The ratio between the pressure drop in the fine tubular element and the pressure drop in the tubular extension is for example greater than 100.

The body of the flask is for example tapered in the lower part thereof and the flask is graduated.

According to a first embodiment, the device includes for example a lateral appendix provided with a central channel opening into the flask, which constitutes the inlet of the flask, a tubular sleeve crossed by the fine tubular element which is provided with seals, the sleeve being engaged in the appendix so that the fine tubular element is housed in the central channel, and second fastening means for holding the sleeve fixed with respect to the flask.

According to another embodiment, the device may also include a lateral appendix provided with a central channel opening into the flask, which constitutes the inlet, a guide sleeve engaged in the central channel, a solid disk made of an elastic material and a cap for holding the disk against the flask inlet, the fine tubular element (such as a hollow needle) being engaged along the guide sleeve through the disk.

The device may further include cooling means such as a vessel for a cooling substance, adapted for containing at least part of the flask for example.

The layout of the device is such that the pressure drop occurs in the fine tubular dement at the flask inlet, the pressure in the rest of the cell never being higher than some bars (typically 5 bars), whereas the pressures of the fluids to be transferred from the containment cell are commonly higher than 100 bars. The outlet tube in the upper part of the flask is relatively wide and the ratio between the pressure drops occurring at the inlet and the corresponding pressure drops at the outlet is commonly greater than 100. The cell may therefore be made of glass without any risk of bursting, even if drawing off is achieved rapidly, with all the advantages following therefrom: transparency, easy manufacturing (sealed connections may be easily achieved by welding) and moderate manufacturing cost.

The separation of the phases of a sample of fluids obtained with the device according to the invention is a particularly good separation because the eddy or cyclone caused by the tangential injection tends to eject the liquid (or liquefied through cooling) phase droplets towards the periphery of the flask, thus preventing them from being driven towards the outlet by the motion of the gas phase.

Besides, the cyclone effect is achieved in transient state on a limited sample volume and without drawing off of the denser phase through the bottom of the flask.

BRIEF DESCRIPTION OF THE DRAWINGS

Other features and advantages of the device according to the invention will be clear from reading the description hereafter of an embodiment given by way of non limitative examples, with reference to the accompanying drawings in which:

FIG. 1 diagrammatically shows a section of the separator flask,

FIG. 2 diagrammatically shows how the fluid inlet tube is offset with respect to the axis of the flask which allows the cyclone effect helping towards the good separation of the phases to be obtained.

DESCRIPTION OF THE PREFERRED EMBODIMENTS

Figure 3:
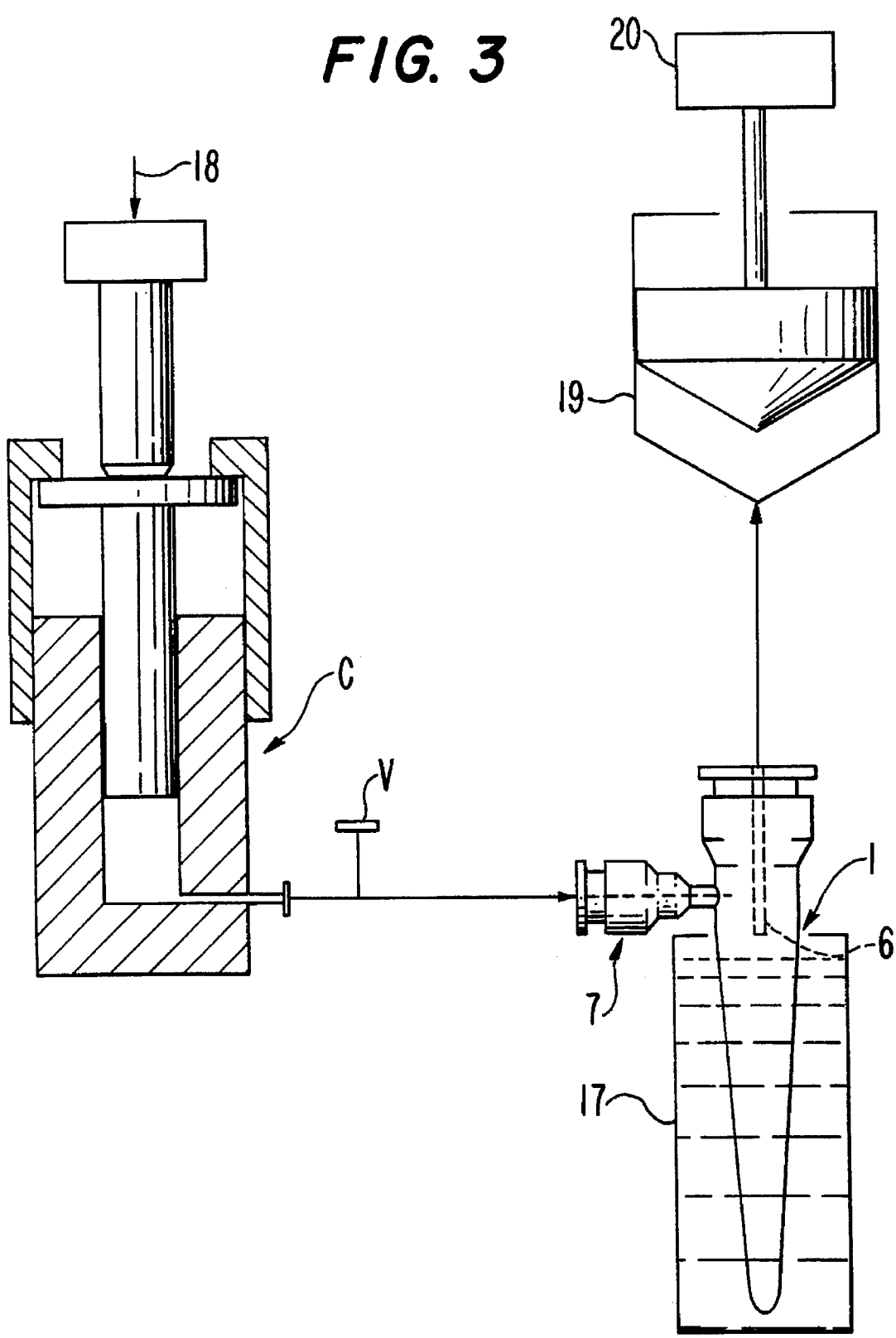
FIG. 3 shows an example of application of the device.

The separator flask according to the invention includes a tapered body 1 made of a transparent material, for example cone-shaped towards the base thereof, which is ended at its opposite end by a head 2 provided with a thread for screwing in a cap 3. A metallic tube 4 whose section is substantially equal to the inner section of the body in the upper part thereof passes through this cap 3. Tube 4 is driven in this flask and held in position by screwing cap 3 on head 2. Seals 5 are placed around tube 4 close to the end thereof. This tube 4 is extended towards the inside of the body by a tubular extension 6 of smaller section.

The flask includes a hollow lateral appendix 7 for the injection of the fluid sample to be separated, which opens into the body, above the level of the base of tubular extension 6, through a fine channel 8 (FIG. 2). The axis B of the channel is laterally offset with respect to the axis of symmetry A of the flask, so that the fluid flows in for example tangentially with respect to the inner wall of the body. The lateral appendix 7 is ended by a head 9 provided with a thread for screwing in a second cap 10. A tubular metallic sleeve 11, which is crossed along its axis by a line 12 of small section adapted to that of the fine channel 8, passes through this cap 10. Screwing the second cap 10 by means of a joint 13 has the effect of holding the metallic sleeve 11 in position and of engaging line 12 into channel 8 up to the immediate neighbourhood of the inlet port thereof in the body. Seals 14 are placed around line 12 in the neigbourhood of the end thereof so as to minimize the clearance volume. Line 12 is connected eternally to a vessel C containing the fluid sample to be separated, possibly under a very high pressure (100 to 200 MPa for example).

At its end opposite extension 6, tube 4 is associated with a threaded ring 16 allowing it to be connected to a vessel R where the gas phase is to be collected.

The section of line 12 is selected much smaller than that of the outlet line (4, 6) so that, if the fluid from vessel C is at a very high pressure, the near total of the pressure drop undergone thereby is transferred upstream from the separator flask kept at a relatively low pressure (0.5 to 1 MPa for example). As the pressure decline occurs upstream from the flask the separation or demixing of the phases is easier.

The lower part of the flask is preferably graduated in units of volume, which allows direct reading of the volume of liquid phase accumulating at the base.

The sample of multiphase fluid is injected through line 12. The fine channel 8 being offset, the fluid undergoes a centrifugal force which makes it swirl along the inner wall of the flask (cyclone effect). The liquid phase drops thus tend to be flattened against the wall and therefore driven away from the tubular extension 6 in the axis of the flask, through which the gas phase escapes. The amount of liquid which may be carried over by the gas is thus very limited.

The separating device may further include means for cooling the lower part of flask 1. These means consist for example of a vessel 17 containing a cooling substance such as liquid nitrogen. The cooling of the flask promotes the liquefaction of the condensable gases which are carried over towards the lower part of the flask by the centrifugal force.

Figure 4:
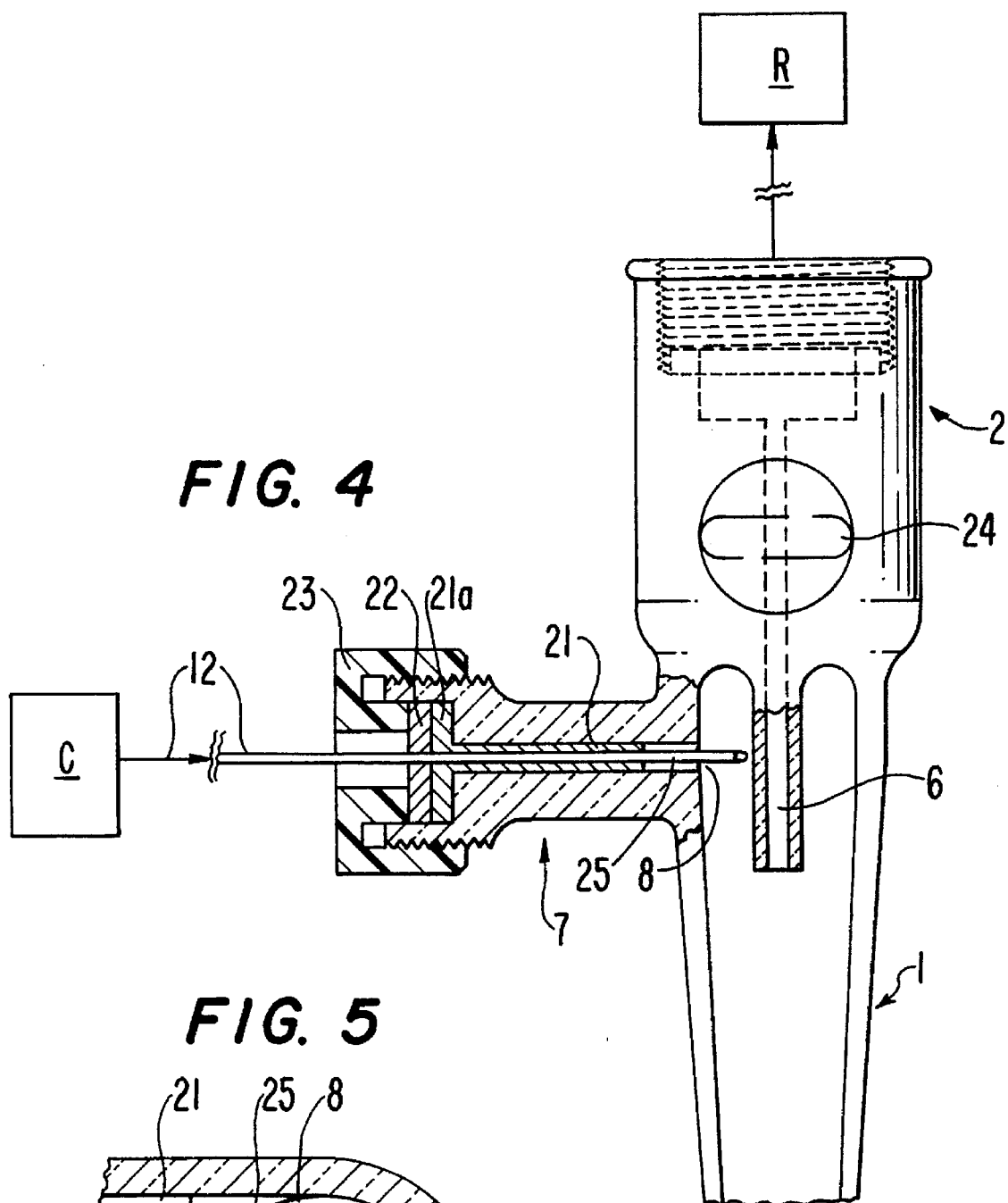
FIGS. 4, 5 show a second embodiment of the separator flask provided with hollow needle injection means.
Figure 5:
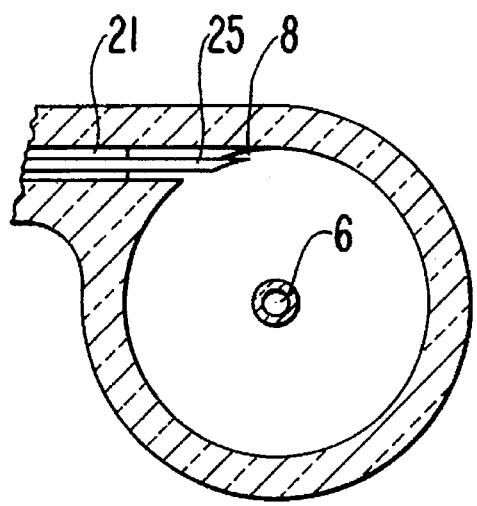

According to the embodiment shown in FIGS. 4, 5, the fine channel 8 is lined, on part of its length, with a sleeve 21 made of a plastic material such as Teflon for example. The end neck of appendix 7 is closed by an elastomer disk or septum 22 which is held in position by a screwed threaded cap 23. Communication between the tubular extension 6 and the tank R for collecting the gaseous fraction of the fluid may be controlled by interposing a valve 24 lodged in the upper part of the body.

The fluid sample is injected by connecting the line 12 coming from vessel C to a hollow needle 25 preferably provided with a beveled end. To perform an injection, needle 25 just has to be driven in along the axis of sleeve 21, up to the neighbourhood of the tubular extension 6, through disk 22.

This embodiment is advantageous because it simplifies the operations for communicating vessel C with the separator flask and their separation, the removal of the needle isolating the flask again. Furthermore, the fineness of the central channel of needle 25 is favourable for obtaining a very high pressure drop at the inlet of the flask, as already stated.

The device for separating phases according to the invention may notably be used for separating the phases of fluid samples kept at high temperatures (between 0° C. and 200° C. for example) and high pressures (over 100 MPa for example) and which are expanded in order to be analyzed, as described in patent application FR-EN-93/07,077 cited above.

The fluid sample to be separated (FIGS. 3 to 5) is contained in a sampling cell C. By means of a jack 18 and through the control of a valve V, the sample is injected into the preferably cooled separator flask 1 so as to collect at the base the liquid phase and possibly solid deposits. The gaseous fraction of the sample, escaping through tube 6, is collected in a gasometer 19 kept under constant pressure through a pressure-controlled motor 20.

We claim:

1. A cyclone separating device for separating a gas phase from a liquid phase in a fluid sample kept under high pressure of at least 100 MPa in a cell, said device including a flask made of transparent material, said flask comprising a body provided with a tubular side inlet integrally formed with the body, said side inlet being connected with said cell for injecting the sample into the flask, said side inlet being laterally offset with respect to an axis of symmetry of the body of the flask so as to obtain a cyclone effect on the injected sample, and said body also being provided with an upper port for the escape of the gas phase from the flask, said device further comprising a fine tubular element extending within said tubular side inlet and communicating at a first end with the inside of the flask and at another end with said cell via said side inlet, wherein an inner section of the said tubular element is selected to be smaller with respect to an inner section of said upper port so that almost the total pressure drop undergone by the injected sample occurs along the tubular element, the remaining pressure of the fluid sample after said pressure drop being low enough to allow the flask to be made of said transparent material and a tube provided with seal means, which is engaged in said upper port and extended towards the inside of the flask by a tubular extension arranged substantially along an axis of the body of the flask, a section of the tubular extension being large enough to result in a pressure drop therethrough which is negligible with respect to the pressure drop in said fine tubular element, and means for fastening the tube to the body of the flask; the ratio between the pressure drop in the fine tubular element and the pressure drop in the tubular extension being greater than 100.

2. A device according to claim 1, wherein the transparent material is glass.

3. A device as claimed in claim 1, wherein said flask is provided with a body which is tapered in the lower part thereof and is graduated.

4. A device as claimed in claim 1, further including means for cooling the flask.

5. A device as claimed in claim 1, further including means for cooling the flask, said cooling means including a vessel for containing a cooling substance and adapted to contain at least a lower part of the flask.

6. A device as claimed in claim 1, further including means for connecting an outlet of the upper port to a vessel kept at a substantially constant pressure for the reception of the separated gas phase.

7. A cyclone separating device for separating a gas phase from a liquid phase in a fluid sample kept under high pressure of at least 100 MPa in a cell, said device including a flask made of transparent material, said flask comprising a body provided with a side inlet in a hollow appendix integrally formed with the body for injecting the fluid sample, said hollow appendix being provided with a central channel opening into the body of said flask and laterally offset with respect to an axis of symmetry of the body of the flask so as to obtain a cyclone effect on the injected sample, said body of the flask being provided with an upper port for escape of the gas phase from the flask, said device also comprising a guide sleeve positioned in the central channel, a disk made of an elastomeric material closing the side inlet and fastening means for securing the disk and sleeve with respect to the side inlet, a fine tubular element communicating at a first end with said cell and penetrating through said disk and extending inside the flask, with said guide sleeve guiding said tubular element, an inner section of the tubular element being selected to be smaller with respect to an inner section of said upper port so that almost the total pressure drop undergone by the injected sample occurs along the fine tubular element, the remaining pressure of the fluid sample after said pressure drop being low enough to allow the flask to be made of a transparent material, and a tube provided with seal means, which is engaged in said upper port and extended towards the inside of the flask by a tubular extension arranged substantially along the axis of the body of the flask, a section of the tubular extension being large enough to result in a pressure drop therethrough which is negligible with respect to the pressure drop in said fine tubular element, and means for fastening the tube to the flask; the ratio between the pressure drop in the fine tubular element and the pressure drop in the tubular extension being greater than 100.

8. A device as claimed in claim 7, wherein the fine tubular element is a thin removable hollow needle with a sharp end for piercing said disk, said needle providing a large pressure drop for the injected fluid sample.

9. A device as claimed in claim 7, wherein said flask is provided with a body which is tapered in the lower part thereof and is graduated.

10. A device as claimed in claim 8, wherein said flask is provided with a body which is tapered in the lower part thereof and is graduated.

11. A device as claimed in claim 7, further including means for cooling the flask.

12. A device as claimed in claim 8, further including means for cooling the flask.

13. A device as claimed in claim 7, further including means for cooling the flask, said cooling means including a vessel for containing a cooling substance and adapted to contain at least a lower part of the flask.

14. A device as claimed in claim 8, further including means for cooling the flask, said cooling means including a vessel for containing a cooling substance and adapted to contain at least a lower part of the flask.

15. A device as claimed in claim 7, further including means for connecting an outlet of the upper port to a vessel kept at a substantially constant pressure for the reception of the separated gas phase.

16. A device as claimed in claim 8, further including means for connecting an outlet of the upper port to a vessel kept at a substantially constant pressure for the reception of the separated gas phase.

17. A device according to claim 7, wherein the transparent material is glass.

18. A device according to claim 7, wherein said tubular element comprises a thin hollow needle with a beveled end suitable for being inserted through the elastic disk closing the side inlet.

19. A device according to claim 7, wherein a valve is located in an upper portion of the flask to control flow of gas through said tubular extension.

* * * * *